United States Patent
Modi et al.

(10) Patent No.: US 9,708,258 B2
(45) Date of Patent: Jul. 18, 2017

(54) INDOLE 3-CARBINOL DERIVATIVES

(71) Applicant: Cadila Pharmaceuticals Ltd, Bhat, Ahmedabad (IN)

(72) Inventors: Rajiv Indravadan Modi, Ahmedabad (IN); Chandan Hardhan Singh, Ahmedabad (IN); Niravkumar Sureshbhai Sagar, Ahmedabad (IN); Sunilkumar Ramsuratbhai Tivari, Ahmedabad (IN); Bipin Dhanajibhai Gadhiya, Ahmedabad (IN)

(73) Assignee: Cadila Pharmaceuticals, Ltd. (IN)

( * ) Notice: Subject to any disclaimer, the term of this patent is extended or adjusted under 35 U.S.C. 154(b) by 0 days.

(21) Appl. No.: 14/904,734

(22) PCT Filed: Jul. 11, 2014

(86) PCT No.: PCT/IB2014/063031
§ 371 (c)(1),
(2) Date: Jan. 19, 2016

(87) PCT Pub. No.: WO2015/008202
PCT Pub. Date: Jan. 22, 2015

(65) Prior Publication Data
US 2016/0159740 A1 Jun. 9, 2016

(30) Foreign Application Priority Data
Jul. 16, 2013 (IN) .......................... 2370/MUM/2013

(51) Int. Cl.
*C07D 209/26* (2006.01)
*C07D 209/12* (2006.01)

(52) U.S. Cl.
CPC ......... *C07D 209/26* (2013.01); *C07D 209/12* (2013.01)

(58) Field of Classification Search
CPC ............................. C07D 209/26; C07D 209/12
See application file for complete search history.

(56) References Cited

U.S. PATENT DOCUMENTS 7,807,705 B2  10/2010  Chen et al.

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Inflammation [online], retrieved from the internet on Feb. 7, 2017. URL http://www.medicalnewstoday.com/articles/248423.php.*
Liu et al., "Aerobic oxidation of indole carbinols using $Fe(NO_3)_3$ $9H_2O$/TEMPO/NaCl as catalysts," *Org. Biomol. Chem.*, 11(25) 9 pages (2013).
Tricotet et al., "Automated Generation and Reactions of 3-Hydroxymethylindoles in Continuous-Flow Microreactors," *Chem. Eur. J.*, 16(22):6678-6686 (2010).
Kitahara et al., "Steroisomers of monatin, their use as sweeteners, and preparation of of them and their intermediates," Database CA [Online] Chemical Abstracts Service, Columbus, Ohio, US; 3 pages, Feb. 26, 2002, XP-002730673.
Sharma et al, "Biological Importance of the Indole Nucleus in Recent Comprehensive Years: A Review," *Journal of Heterocyclic Chemistry*, 47(3):491-502 (2010).
International Search Report and Written Opinion for International Application No. PCT/IB2014/063031, mailed on Oct. 29, 2014, 9 pages.

* cited by examiner

*Primary Examiner* — Shawquia Jackson
(74) *Attorney, Agent, or Firm* — Burns & Levinson, LLP

(57) ABSTRACT

The present invention relates to novel stable indole-3-carbinol derivatives of Formula-I and its pharmaceutical composition and biological activity. The present invention includes compositions and methods for the treatment and prevention of conditions associated with Inflammation.

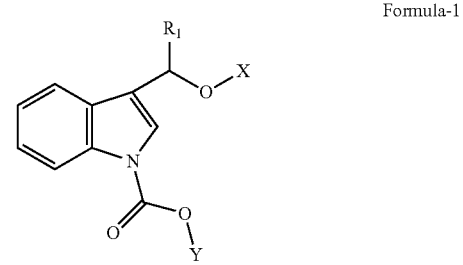

Formula-1

11 Claims, 3 Drawing Sheets

INDOLE 3-CARBINOL DERIVATIVES

CROSS REFERENCE TO RELATED APPLICATION

This is a §371 U.S. National Stage of PCT Application No. PCT/IB2014/063031, filed Jul. 11, 2014, which was published in English under PCT Article 21(2) as WO2015008202 A1 on Jan. 22, 2015, which in turn claims the benefit of and priority to the Indian Application No. IN 2370/MUM/2013, filed on Jul. 16, 2013, each of which is incorporated by reference herein in its entirety.

FIELD OF THE INVENTION

The present invention relates to novel stable indole-3-carbinol compounds and its pharmaceutical composition and biological activity. More particularly, the invention pertains to novel stable indole-3-carbinol compounds having potent anti-inflammatory activity.

BACKGROUND OF THE INVENTION

Inflammation is a complex biological process that occurs in response to stimuli including, for example, infection, damage to cells and/or tissue, irritants, etc. While inflammation is vital for healing and combating infection, abnormal or excessive inflammation can adversely affect the health, comfort and/or mobility of a subject.

Many people worldwide are affected by inflammatory diseases or disorders such as acute or chronic idiopathic inflammatory arthritis, psoriasis, chronic dermatosis, myositis, demyelinating diseases, chronic obstructive pulmonary disease (COPD)$_1$ interstitial lung disease, glomerulonephritis, interstitial nephritis, chronic active hepatitis, Crohn's disease, ulcerative colitis, plaque formation in atherosclerosis, degenerative diseases of the joints or nervous system, or multiple sclerosis (MS). Populations are ageing and an increasing number of people require medication for age-related inflammatory diseases.

A wide range of anti-inflammatory agents are known including steroids (such as glucocorticoids). In many cases these drugs are not as effective at treating some inflammatory conditions and/or also associated with adverse side effects. Long term use of steroids gives rise to chronic side effects, including immunosuppression, tissue wasting and loss of bone density.

Another well-known class of anti-inflammatory pharmaceuticals is the non-steroidal anti-inflammatory drugs (NSAID). The primary mode of action of known NSAIDs is through inhibition of the COX enzyme, which results in the inhibition of prostaglandin synthesis.

The NSAIDs currently in the marketplace provide some alternative to steroid-based treatments. However, administration of NSAIDs can cause highly undesirable side effects such as gastro-intestinal bleeding, ulcers and renal disease. In certain cases, these drugs do not provide effective relief for some sufferers of inflammatory disease.

Monoclonal antibody drugs such as Infliximab, Etanercept and Adalimumab are useful as anti-inflammatory agents, but have drawbacks such as route of administration (only parenteral), high cost and activation of latent tuberculosis. (Rheumatology, 2007, 46(5): 887-888, Clin. Infect. Dis., 39: 295-299 and Ann. Rheum. Dis., 64 (Suppl III): 86)

Some current anti-inflammatory agents have adverse side effects which include any one or more of gastrointestinal tract damage, renal damage, photosensitivity, hepatic stimulation, headaches, dizziness, Crushing's syndrome, hypertension, hypokalemia, hypernatremia, etc. Furthermore, due to adverse reactions some anti-inflammatory agents are not suitable for some subjects including, for example, pregnant subjects and subjects with an inflammatory bowel disease. Adverse side-effects of anti-inflammatory agents can result from topical, oral or other forms of administration. Due to the limitations of many current anti-inflammatory drugs, there is a continual need to develop new anti-inflammatory agents.

The discovery of indomethacin, ethodolac and tenidap, as potent anti-inflammatory agents, has led to the exploration of indole nucleus. Indole derivatives have been found to possess potent wide spectrum of biological activities especially antibacterial, antifungal, anti-inflammatory and analgesic. Further, it has been reported that substitution of different heterocyclic or aromatic moieties at 2 or 3-position of indole nucleus modulates the anti inflammatory activity of such substituted indole derivatives.

The natural product indole-3-carbinol (I3C; found in vegetables of the genus *Brassica*) is a promising inflammatory prevention or therapy agent. As an anti-inflammatory compound, I3C suppresses inflammation and decreases the production of inflammatory cytokines known to be involved in initiating the inflammatory cascade. Furthermore, I3C has been shown to prevent the initiation of inflammatory responses at a very early stage by acting directly at the molecular level. Indole-3-carbinol has emerged as a promising chemo preventive agent due to its in vivo efficacy in various animal models.

U.S. Pat. No. 8,153,680 discloses alkyl indole-3-carbinol derivatives which can treat different cancers, including but not limited to prostate cancer, breast cancer, leukemia, non-small cell lung cancer, colon cancer, CNS cancer, melanoma, ovarian cancer, and renal cancer.

U.S. Pat. No. 7,807,705 also discloses novel indole-3-carbinol derived antitumor agents which exhibit unique ability to target multiple molecular defects clinically relevant to oncogenesis and tumor progression.

Weng et al discloses Indole-3-carbinol and its metabolite 3,3'-diindoylmethane (DIM) target multiple aspects of cancer cell cycle regulation and survival including Akt-NFκB signaling, caspase activation, cyclin-dependent kinase activities, estrogen metabolism, estrogen receptor signaling, endoplasmic reticulum stress, and BRCA gene expression (Cancer Lett. 2008 Apr. 18; 262(2): 153)

A major complication in interpreting the physiological results is that Indole-3-carbinol is extremely unstable in acidic solution and it does not completely survive exposure to gastric acid. Sensitive analytical methods reveal that Indole-3-carbinol is converted to several indole derivatives in acid conditions. It is converted into biologically active components such as its dimer 3,3'-diindolylmethane (DIM) and indolo[3,2-b]carbazole (ICZ) through an acid-catalyzed reaction occurring in the low-pH environment of the stomach. ICZ is also produced, presumably from the nutritive indole, tryptophan, as a metabolic product of intestinal bacteria.

Although indole-3-carbinols are potent anti-cancer agents which are having multiple side effects with respect to dosage and administration they also posses potent anti-inflammatory activity. The present study is directed to prepare novel stable indole-3-carbinol derivatives having anti-inflammatory activity which are stable in vitro and vivo conditions The present invention is also directed to prepare novel stable indole-3-carbinol as a scaffold to carry out structural modifications in order to achieve anti-inflammatory agents that are distinct in comparison to native indole-3-carbinol and its metabolites.

OBJECT OF THE INVENTION

An object of the present invention is to provide novel stable indole-3-carbinol derivatives of Formula-1 or pharmaceutically acceptable salts thereof.

Yet another object of the present invention is to provide a process for the preparation of novel stable indole-3-carbinol derivatives of Formula-1 or pharmaceutically acceptable salts thereof.

Yet another object of the invention described herein is the use of novel stable indole-3-carbinol derivatives of Formula-1 or pharmaceutically acceptable salts thereof for the treatment of inflammatory diseases.

SUMMARY OF THE INVENTION

The present invention relates to novel indole-3-carbinol compounds of Formula-1 that are potent anti-inflammatory agents.

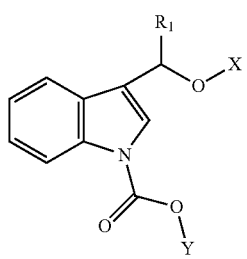

Formula-1 wherein, $R_1$ is selected from hydrogen, aryl, haloaryl;

X is selected from hydrogen or —C(O)$C_nH_{2n+1}$ wherein n is an integer selected from 2 to 16, or —C(O)(CH$_2$)$_m$—COOH wherein m is an integer selected from 2 to 5; Y is selected from alkyl or arylalkyl; or pharmaceutically acceptable salts, derivatives, metabolites thereof.

In another embodiment the present invention provides a process for the preparation of novel stable indole-3-carbinol derivatives of Formula-1 or pharmaceutically acceptable salts thereof which comprises the following steps:

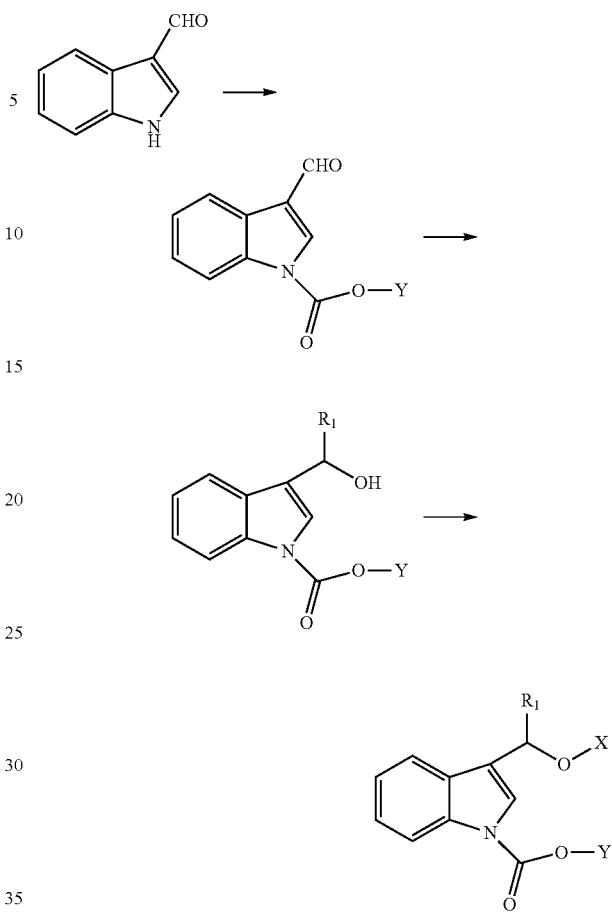

i. Reacting compound of formula-IIa

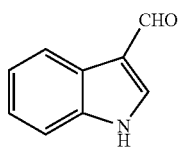

Formula-IIa with Y—O—CO—Cl or Y—CO—O—CO—Y to provide compound of formula-II; wherein Y is as defined above.

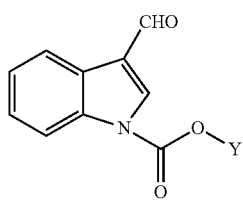

Formula-II ii. Reacting compound of formula-II with reducing agent or $R_1$Mg halide to provide compound of formula-III wherein $R_1$ and Y are defined above.

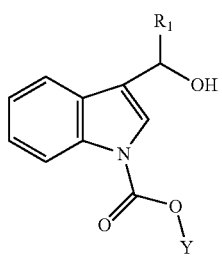

Formula-III iii. Reacting compound of formula-III with acid halide or acid anhydride or acid to provide compound of formula-1; wherein $R_1$, X and Y are as defined above.

In another embodiment the present invention provides pharmaceutical compositions of novel stable indole-3-carbinol derivatives of Formula-1 or pharmaceutically acceptable salts thereof and a pharmaceutically acceptable excipient.

In another embodiment of the present invention the conditions for the preparation of compounds of formula-1, II, IIa, III are illustrated in examples.

In another embodiment, the invention relates to the use novel indole-3-carbinol derivatives, to target multiple pathways associated with inflammatory diseases.

DETAILED DESCRIPTION OF THE INVENTION

Figure 1:
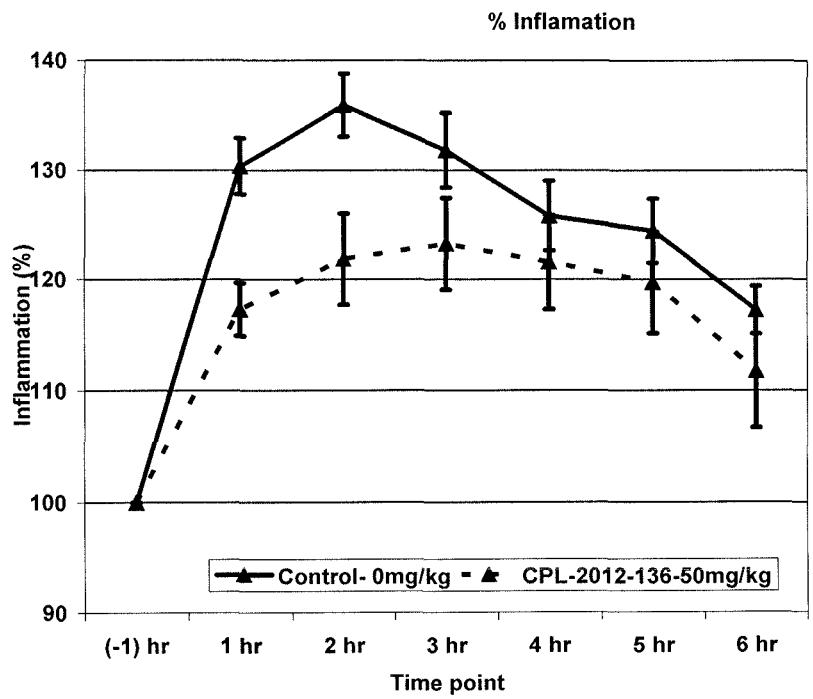
FIG. 01: Anti-inflammatory screening results of CPL-2012-136
Figure 2:
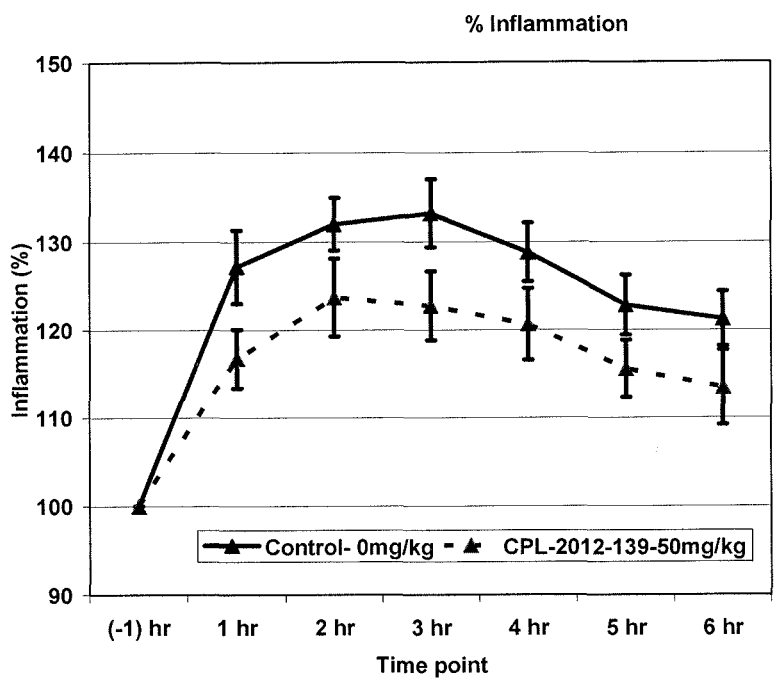
FIG. 02: Anti-inflammatory screening results of CPL-2012-139
Figure 3:
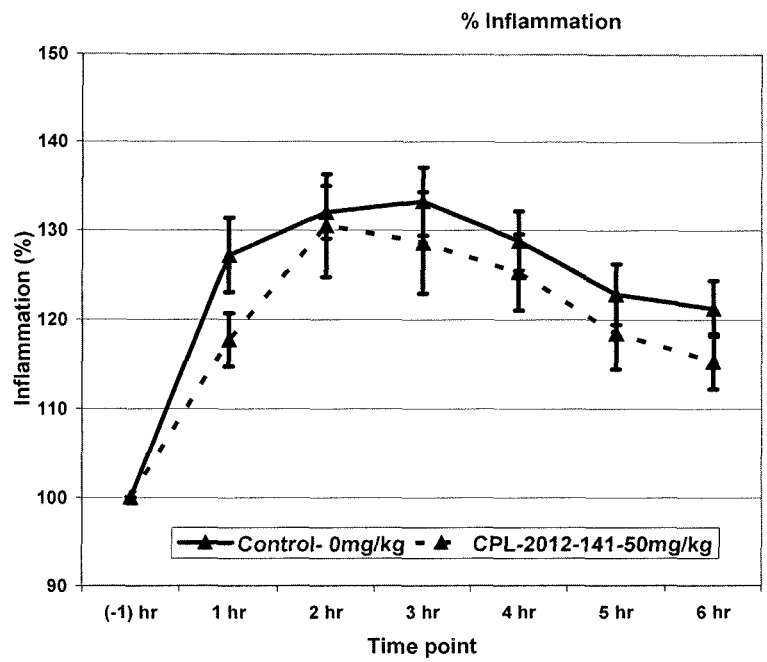
FIG. 03: Anti-inflammatory screening results of CPL-2012-141
Figure 4:
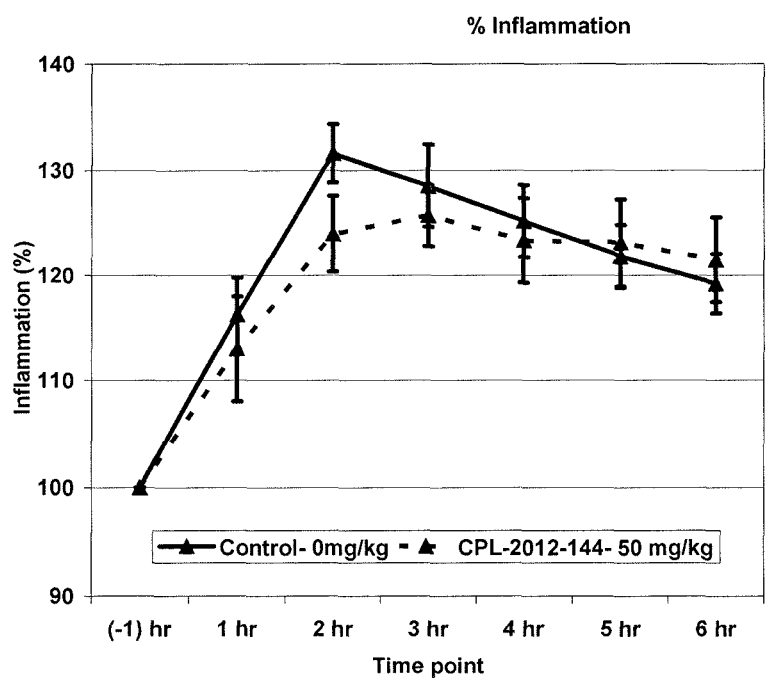
FIG. 04: Anti-inflammatory screening results of CPL-2012-144
Figure 5:
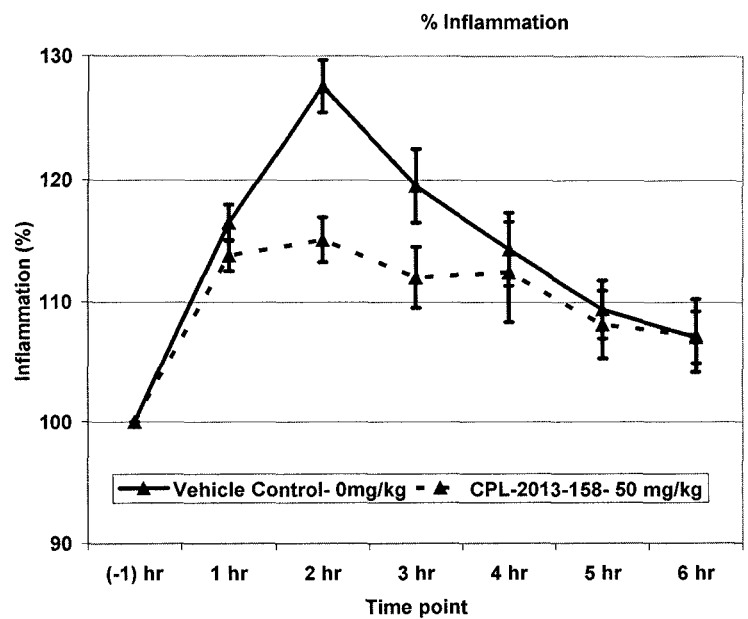
FIG. 05: Anti-inflammatory screening results of CPL-2013-158
Figure 6:
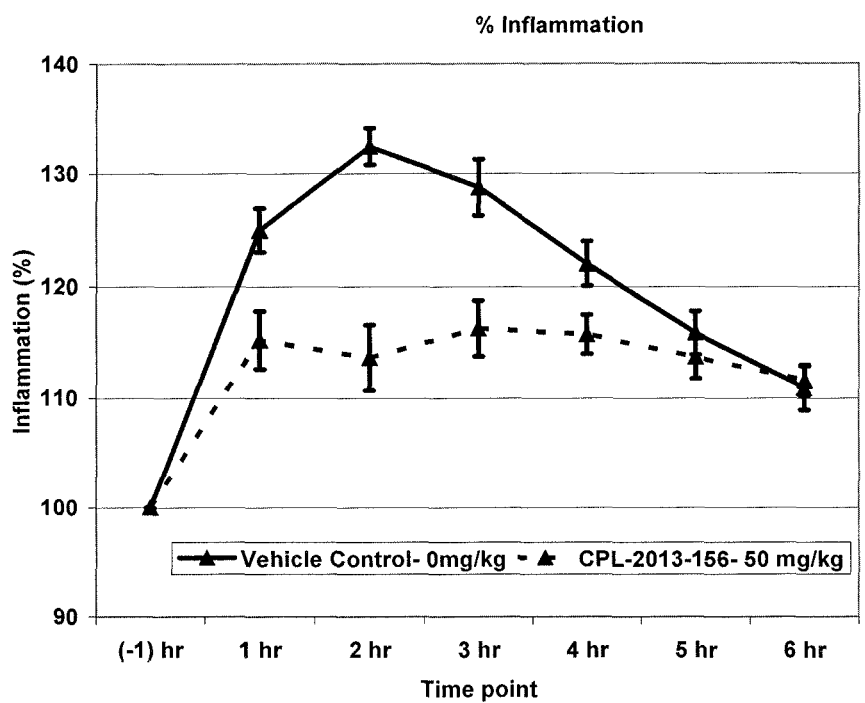
FIG. 06: Anti-inflammatory screening results of CPL-2013-156

In one embodiment the invention relates to a novel indole-3-carbinolderivatives of Formula-1.

Formula-1 wherein,
$R_1$ is selected from hydrogen, aryl, haloaryl;
X is selected from hydrogen or —C(O)$C_nH_{2n+1}$ wherein n is an integer selected from 2 to 16 or —C(O)(CH$_2$)$_m$—COOH wherein m is an integer selected from 2 to 5; Y is selected from alkyl or arylalkyl;

or pharmaceutically acceptable salts, derivatives, metabolites thereof.

Compound of Formula-1 is further elaborated to explain the invention in detail:

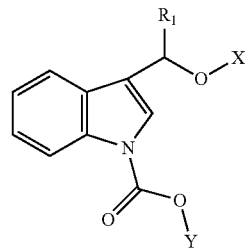

Formula-1

| Compound | $R_1$ | X | Y |
|---|---|---|---|
| CPL-2012-128 | H | —C(O)$C_{15}H_{31}$ | —$C_4H_9$ |
| CPL-2012-136 | H | —C(O)(CH$_2$)$_2$—COOH | —$C_4H_9$ |
| CPL-2012-139 | H | —C(O)$C_2H_5$ | —$C_4H_9$ |
| CPL-2012-141 | H | —C(O)$C_3H_7$ | —$C_4H_9$ |
| CPL-2012-144 | H | —C(O)$C_4H_9$ | —$C_4H_9$ |
| CPL-2013-155 | —$C_6H_5$ | —C(O)$C_2H_5$ | —$C_4H_9$ |
| CPL-2013-156 | —$C_6H_2F_3$ | H | —$C_4H_9$ |
| CPL-2013-157 | —$C_6H_2F_3$ | —C(O)$C_2H_5$ | —$C_4H_9$ |
| CPL-2012-158 | H | —C(O)$C_2H_5$ | —$C_7H_7$ |
| CPL-2012-159 | H | —C(O)$C_6H_{13}$ | —$C_4H_9$ |

Some specific examples to demonstrate the embodiment include following novel indole-3-carbinol derivatives without limiting the scope of the invention:

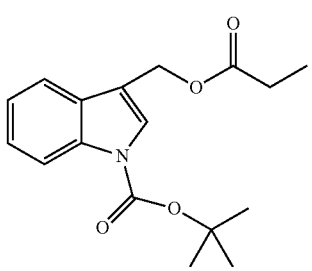

CPL-2012-139

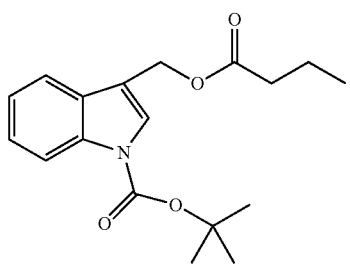

CPL-2012-141

CPL-2012-144

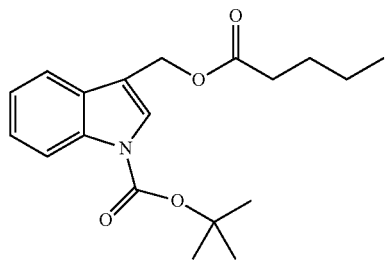

CPL-2012-159

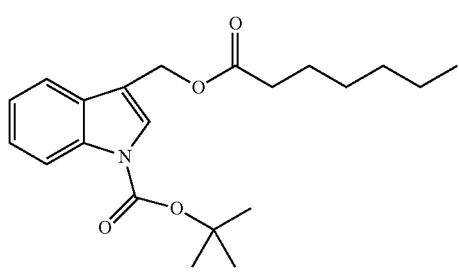

CPL-2012-128

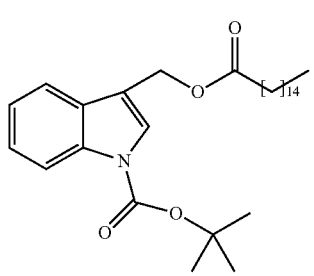

CPL-2012-158

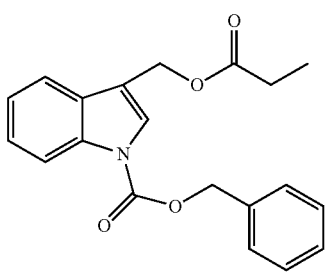

CPL-2012-156

CPL-2012-136

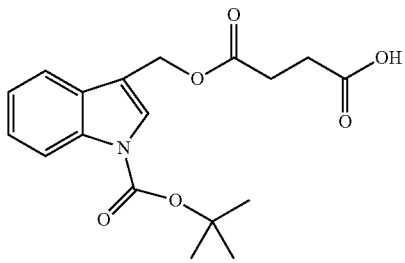

CPL-2012-155

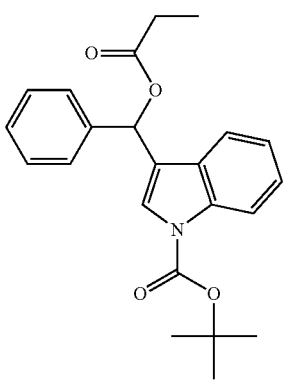

CPL-2012-157

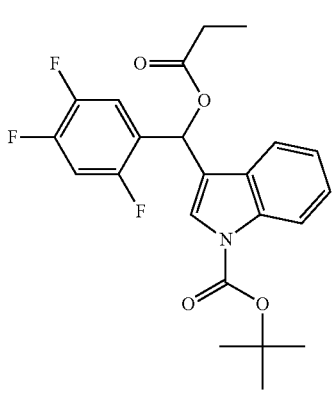

and pharmaceutically acceptable salts, derivatives or metabolites thereof.

In one exemplary embodiment, wherein formula-1 is further defined as

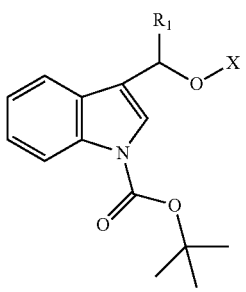

wherein $R_1$ is hydrogen and X is $-C(O)C_nH_{2n+1}$ wherein n is an integer selected from 2 to 16 or pharmaceutically acceptable salts, derivatives, metabolites thereof.

In another exemplary embodiment, where in formula-1 is further defined as

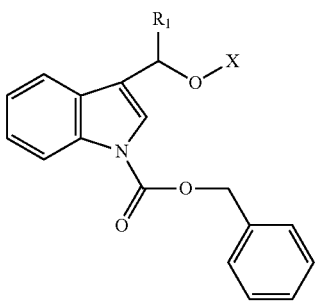

wherein $R_1$ is hydrogen and X is —C(O)$C_nH_{2n+1}$ wherein n is an integer selected from 2 to 16 or pharmaceutically acceptable salts, derivatives, metabolites thereof. In another exemplary embodiment, where in formula-1 is further defined as

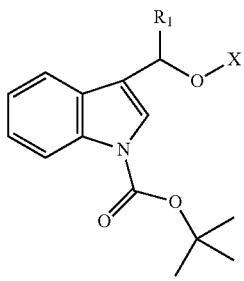

wherein $R_1$ is hydrogen and X is —C(O)(CH$_2$)$_m$—COOH wherein m is an integer selected from 2 to 5. or pharmaceutically acceptable salts, derivatives, metabolites thereof.

In another exemplary embodiment, wherein formula-1 is further defined as

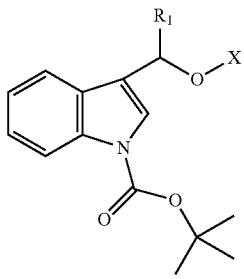

wherein $R_1$ is selected from aryl or haloaryl and X is —C(O)$C_nH_{2n+1}$ wherein n is an integer selected from 2 to 16; or pharmaceutically acceptable salts, derivatives, metabolites thereof.

In another exemplary embodiment, where in formula-1 is further defined as

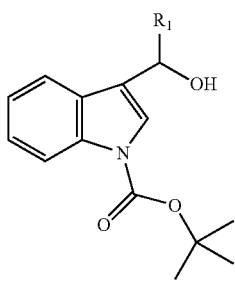

wherein $R_1$ is selected from aryl or haloaryl; or pharmaceutically acceptable salts, derivatives, metabolites thereof.

The compound of general formula-II is obtained by the generalized process as depicted below:

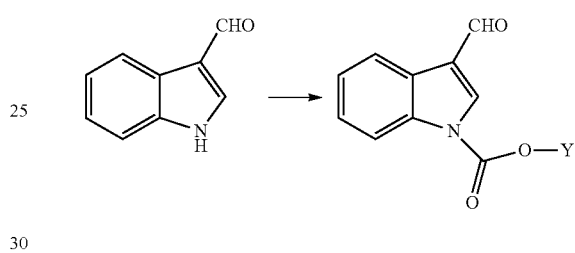

reacting a compound of general Formula-IIa with Y—O—CO—Cl or Y—CO—O—CO—Y to yield general formula-II where in Y is as defined above.

The compound of general formula-III is obtained by the generalized process as depicted below:

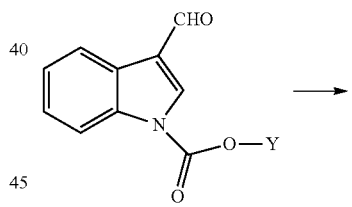

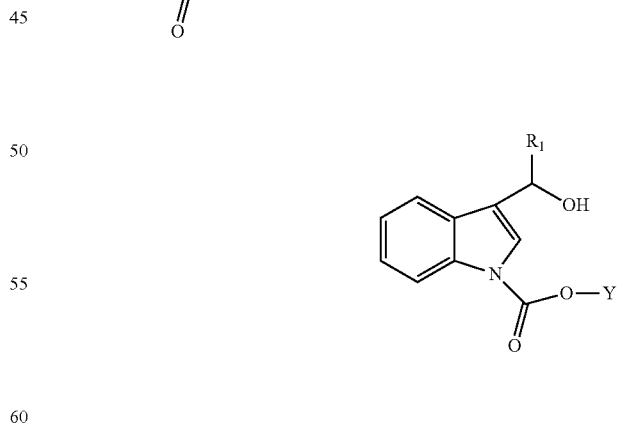

reacting a compound of general Formula-II with a reducing agent or $R_1$Mg halide to yield general formula-III where in Y is as defined above.

The compounds of general Formula-I is obtained by the generalized process as depicted below:

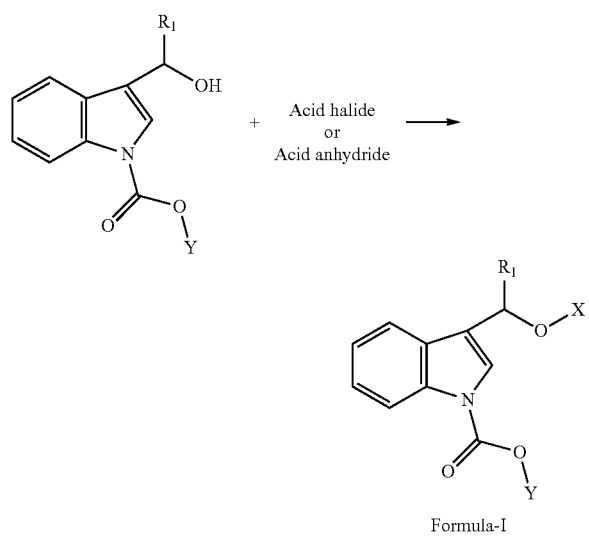

Formula-I reacting a compound of general Formula-III

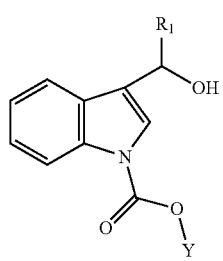

wherein $R_1$ is hereinbefore defined and Y denotes a alkyl or arylalkyl with acid halide or acid anhydride in the presence of base to yield a general Formula-1.

The reaction is expediently carried out in a solvent such as tetrahydrofuran, dioxane, dimethylformamide, dimethylsulphoxide, ethyleneglycol monomethylether, ethyleneglycol, diethylether or sulpholane, optionally in the presence of an inorganic or tertiary organic base e.g. sodium carbonate, potassium carbonate or potassium hydroxide, a tertiary organic base, e.g. triethylamine, or in the presence of N-ethyl-diisopropylamine (Hünig base), while these organic bases is also serve as solvent, and optionally in the presence of esterification catalyst such as Dimethyl amino pyridine at temperatures between 0 to 40° C. The reaction can also be carried out without a solvent.

Alternatively the compounds of general Formula-I are obtained by the generalized process as depicted below:

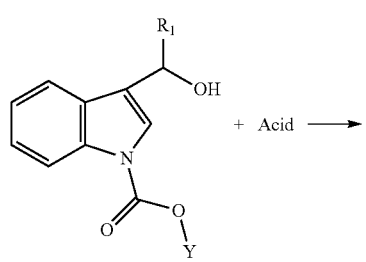

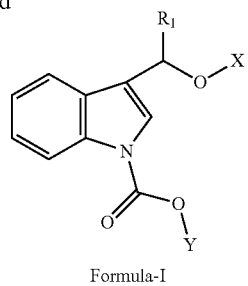

Formula-I reacting a compound of general formula-III

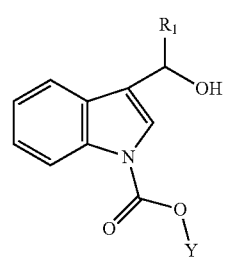

wherein,
$R_1$ is hereinbefore defined and Y denotes a alkyl or arylalkyl group, with acid in the presence of base where in acid is hereinbefore defined to yield a general Formula-I The reaction is expediently carried out in a solvent such as Tetrahydrofuran, dioxane optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of esterification catalyst such as Dimethyl aminopyridine at temperatures between 0 to 40° C. The reaction may, however, also be carried out without a solvent.

Moreover, the compounds of general Formula-I obtained may be resolved into their enantiomers and/or diastereomers, as mentioned hereinbefore. Thus, for example, cis/trans mixtures may be resolved into their Cis and Trans isomers, and compounds with at least one optically active carbon atom may be separated into their enantiomers.

Thus, for example, the cis/trans mixtures may be resolved by chromatography into the cis and trans isomers thereof, the compounds of general Formula-I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general Formula I with at least 2 asymmetric carbon atoms may be resolved into their diastereomers on the basis of their physical-chemical differences using methods known per se, e.g. by chromatography and/or fractional crystallization, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

The synthesized compounds are intended to encompass any compounds which are structurally related to the compounds of Formula I which possess the substantially equivalent activity, as measured by known the derivative of indole-3-carbinol ability to induce apoptosis in rapidly proliferating cells without substantial COX-2 inhibition. By way of example, such compounds may include, but are not limited to, prodrugs thereof. Such compounds can be formed in vivo, such as metabolic mechanism.

Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention.

The term "alkyl", is selected from $C_2$-$C_6$ used either alone or in attachment with another group refers to a saturated aliphatic hydrocarbon radical having the indicated number of carbon atoms and that is unsubstituted or optionally substituted. Alkyl may be a straight chain or a branched chain examples include ethyl, propyl, isopropyl, butyl, tert-butyl, pentyl and hexyl.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth.

The term "aryl" refers to an aromatic group for example, which is a 6 to 10 membered monocyclic or bicyclic ring system, which may be unsubstituted or substituted. Representative aryl groups may be phenyl, naphthyl and the like. When said ring is substituted, the substituents are selected from halogen (e.g., F, Cl, Br, I), hydroxy, alkoxy, nitro, carboxylic acid, $CF_3$, $NHSO_2$alkyl, NHCOalkyl, alkyl, alkenyl, alkynyl, cycloalkyl and acyl.

The term "Alkylaryl" or "arylalkyl" refers to alkyl-substituted aryl groups such as butylphenyl, propylphenyl, ethylphenyl, methylphenyl, 3,5-dimethyl phenyl, tert-butylphenyl and so forth.

The term "Haloaryl" refers to aryl radicals in which one or more substitutable positions has been substituted with a halo radical, examples include fluorophenyl, 4-chlorophenyl, 2,4,5-Tri-Fluorophenyl, 1-Bromo-2,4,5-trifluorobenzene and so forth.

The term "halogen" or "Halide" refers to fluorine, chlorine, bromine and iodine.

Also included in the family of compounds of Formula-I and the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of Formula-I may be prepared from an "Acid" wherein the acid is selected from inorganic acid or from an organic acid. Examples of such "inorganic acids" are hydrochloric, hydrobromic, hydroiodic, nitric, carbonic, sulfuric, and phosphoric acid.

Appropriate "organic acids" may be selected from aliphatic, cycloaliphatic, aromatic, aralphatic, heterocyclic, carboxylic, and sulfonic classes of organic acids, examples of which include formic, acetic, propionic, succinic, butyric, valeric, palmitic heptanoic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, pamoic, methanesulfonic, ethanesulfonic, benzenesulfonic, pantothenic, 2-hydroxyethanesulfonic, toluenesulfonic, sulfanilic, cyclohexyl-aminosulfonic, stearic, algenic, hydroxybutyric, and galacturonic acids.

Appropriate "acid anhydride" that may used include but not limited to acetic anhydride, succinic anhydride, propionic anhydride, valeric anhydride, Heptanoic anhydride.

Appropriate "acid halide" that may used include but not limited to Acetyl chloride, Palmitoyl chloride.

The base used in the reaction is an organic base or an inorganic base. Suitable organic bases that may be used, but are not limited to triethylamine, tributylamine, diisopropylethylamine (DIPEA), triisopropylamine, N-methyl morpholine, pyridine, In one embodiment the organic base is Triethylamine (TEA)

Suitable inorganic bases used for isolation that may be used include, but are not limited to: alkali metal hydroxides such as lithium hydroxide, sodium hydroxide, potassium hydroxide, or the like; carbonates of alkali metals such as sodium carbonate, potassium carbonate, lithium carbonate, or the like; bicarbonates of alkali metals, such as lithium bicarbonate, sodium bicarbonate, potassium bicarbonate, or the like; ammonia; and any mixtures thereof; In one embodiment the inorganic base is sodium bicarbonate.

The solvent may be the same as selected for use in the reaction, or may differ from the solvent in the reaction and for isolation. Where the solvent differs, it can be chosen from among the solvents defined above, or other commonly-used solvents, such as Dichloromethane, ethyl acetate, methanol, ethanol, isopropanol, Hexane among others. The combined organic solvent can then be evaporated off under suitable conditions, e.g., reduced pressure. The residue is then purified by suitable means, e.g., by silica gel column chromatography, eluting with a suitable solvent, or recrystallization with a suitable solvent (e.g., hexane-MDC, hexane-ethyl acetate, Hexane, among others). Other suitable purification means are known to those of skill in the art. Further, other suitable solvent mixtures and ratios can be readily determined by one of skill in the art.

Suitable pharmaceutically acceptable base addition salts of compounds of Formula-I include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of Formula I. All of these salts may be prepared by conventional means from the corresponding compounds of Formula-I by reacting, for example, the appropriate acid or base with the compound of Formula-I.

The reaction is effected in presence of a solvent. The solvents that can be used, include, but or not limited to, ethers such as diethyl ether, tetrahydrofuran, ethyleneglycol mono methyl ether, ethylene glycol diethyl ether, methyl tetrahydrofuran, 1,4-dioxane, or the like; aprotic polar solvents such as N,N-dimethylformamide (DMF), dimethylsulfoxide (DMSO), dimethylacetamide (DMA), acetonitrile, sulpholane or the like or mixtures thereof.

The esterification catalyst is selected from Sulphuric acid and Dimethyl aminopyridine. Preferably Dimethyl amino pyridine is used.

The reducing agent is selected from sodium borohydride.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells.

Alternatively, the methods and compositions described herein may be used as adjunct therapy. By way of example, the apoptosis-inducing compounds of the present invention may be administered alone or in conjunction with other antineoplastic agents or other growth inhibiting agents or other drugs or nutrients.

In the context of the present specification, the term "treat" or "treatment" also includes "prophylaxis" unless there are specific indications to the contrary. The term "treat" or "treatment" within the context of the present invention further encompasses to administer a therapeutically effective amount of a compound of the present invention, to mitigate either a pre-existing disease state, acute or chronic, or a recurring condition. This definition also encompasses prophylactic therapies for prevention of recurring condition and continued therapy for chronic disorders.

The invention will be further described by reference to the following detailed examples. These examples are offered to further illustrate the various specific and preferred embodiments and techniques. It should be understood, however, that many variations and modifications can be made while remaining within the scope of the present invention Preparation of Intermediates 3-Formyl-indole-1-carboxylic acid benzyl ester To a stirred solution of Indole-3-carboxaldehyde in THF was added diisopropyl ethyl amine at 0° C. Reaction was maintained at 0° C. for 10 min. To the stirred solution added benzyloxy carbonyl chloride drop wise at 0° C. Reaction mixture was allowed to stir at RT for over night. THF was concentrated and residue was dissolved in sodium bicarbonate solution. Aqueous layer was extracted with ethyl acetate (20 ml×3). The organic layer was washed with brine and dried over sodium sulfate. The crude product was purified by column chromatography (EtOAc:Hexane) to yield 3-Formyl-indole-1-carboxylic acid benzyl ester.

3-Hydroxymethyl-indole-1-carboxylic acid benzyl ester (N-CBZ-Indole-3-OH)

3-Formyl-indole-1-carboxylic acid benzyl ester is dissolved in Ethanol. Sodium borohydride is added in portions at −17° C. for about 1 hr. Reaction was maintained at −17° C. to 13° C. for 1 hr. After completion of the reaction water is added to reaction mass. Solid thus precipitated was filtered and washed with water. Solid thus obtained is purified by column chromatography using (DCM: Methanol) to yield 3-Hydroxymethyl-indole-1-carboxylic acid benzyl ester.

3-Formyl-indole-1-carboxylic acid tert-butyl ester

Indole-3-carboxaldehyde is dissolved in THF and cooled to 0° C. Added Triethyl amine at 0° C. Then added t-butoxy carbonyl anhydride drop wise at 0° C. Maintained the reaction mass at 0° C. for 30 min. Maintained the reaction mass at RT for over night. After completion of the reaction added citric acid solution. Extract the reaction mass with ethyl acetate. Washed the organic layer with water. Dried the organic layer over sodium sulfate. Oragnic layer was concentrated at 40° C. to obtain the crude product. Crude product is purified by column chromatography (Ethyl acetate:Hexane) to yield 3-Formyl-indole-1-carboxylic acid tert-butyl ester.

3-hydroxymethylindole-1-carboxylic acid tert-butyl ester

3-Formyl-indole-1-carboxylic acid tert-butyl ester was dissolved in THF and cooled to 0° C. Added aqueous solution of sodium borohydride drop wise to the reaction mixture at 0° C. Maintained the reaction at 0° C. for 30 min. Reaction was maintained at RT for 2 hrs. To the reaction mixture water is added and extracted with ethyl acetate. Dry the organic layer over sodium sulfate and concentrated at 40° C. Purified the crude product by column chromatography (EtoAc:Hexane) to yield 3-hydroxymethylindole-1-carboxylic acid tert-butyl ester.

3-(Hydroxy-phenyl-methyl)-indole-1-carboxylic acid tert-butyl ester

Magnesium turnings and bromo benzene is dissolved in THF. Slowly cooled the reaction mass to −5 to 0° C. Slowly add solution of 3-Formyl-indole-1-carboxylic acid tert-butyl ester dissolved in THF. Reaction is maintained at 0° C. for 2-3 hrs. Reaction mass is quenched in 10% citric acid solution. Reaction mass is extracted with ethyl acetate. Aqueous layer and organic layer separated. Organic layer is dried over sodium sulfate. Organic layer is concentrated and purified over column chromatography (Hexane) to yield 3-(Hydroxy-phenyl-methyl)-indole-1-carboxylic acid tert-butyl ester.

Example 1:
3-Hexadecanoyloxymethyl-indole-1-carboxylic acid tert-butyl ester [CPL-2012-128]

Charged 3-hydroxymethylindole-1-carboxylic acid tert-butyl ester in to a flask and added N,N-Dimethyl aminopyridine, Triethyl amine and THF at 0° C. Slowly added palmitoyl chloride drop wise and maintained the reaction at 0° C. for 30 minutes. Gradually temperature was raised to 25-30° C. and maintained for 60 hrs. After completion of the reaction, Sodium bicarbonate solution was added to the reaction mixture and stirred well. Reaction mass was extracted with ethyl acetate twice. Wash the organic layer with water and then with aqueous citric acid. Organic layer was dried over sodium sulfate. Concentrated the organic layer at 40° C. Thus obtained residue is chromatographed on silica gel using EtOAc/Hexane as the eluent.

Example 2: Succinic acid mono-(1-tert-butoxycarbonyl-1H-indol-3-ylmethyl) ester [CPL-2012-136]

Charged 3-hydroxymethylindole-1-carboxylic acid tertbutyl ester is added in to a flask and added Dimethyl aminopyridine, Triethyl amine, succinic anhydride and THF at 0° C. Maintained the reaction at 0° C. for 30 minutes. Slowly temperature was raised to 25-30° C. and maintained for 10 hrs. After completion of the reaction added Sodium bicarbonate solution to the reaction mixture and stirred well. Extract the reaction mass with ethyl acetate twice. Wash the organic layer with water and then with aqueous citric acid. Organic layer was dried over sodium sulfate. Concentrated the organic layer at 40° C. Thus obtained residue is chromatographed on silica gel using MDC/Hexane as the eluent.

Example 3:
3-Propionyloxymethyl-indole-1-carboxylic acid tert-butyl ester [CPL-2012-139]

Charged 3-hydroxymethylindole-1-carboxylic acid tert-butyl ester is added in to a flask and added Dimethyl aminopyridine, Triethyl amine, Propionic anhydride and THF at 0° C. Maintained the reaction at 0° C. for 30 minutes. Slowly temperature was raised to 25-30° C. and maintained for 3 hrs. After completion of the reaction added Sodium bicarbonate solution to the reaction mixture and stirred well. Extract the reaction mass with ethyl acetate twice. Wash the organic layer with water and then with aqueous citric acid. Organic layer was dried over sodium sulfate. Concentrated the organic layer at 40° C. Thus obtained residue is chromatographed on silica gel using Hexane as the eluent.

Example 4:
3-Butyryloxymethyl-indole-1-carboxylic acid tert-butyl ester [CPL-2012-141]

Charged 3-hydroxymethylindole-1-carboxylic acid tert-butyl ester is added in to a flask and added Dimethyl amino pyridine, Triethyl amine, THF, Butyric acid. Maintained the reaction for 10 Minutes then added EDC:HCl at 0° C. and maintained the reaction for 30 minutes. Slowly temperature was raised to 25-30° C. and maintained for 3 hrs. After completion of the reaction added Sodium bicarbonate solution to the reaction mixture and stirred well. Extract the reaction mass with ethyl acetate twice. Wash the organic layer with water and then with aqueous citric acid. Organic layer was dried over sodium sulfate. Concentrated the organic layer at 40° C. Thus obtained residue is chromatographed on silica gel using Hexane as the eluent.

Example 5:
3-Pentanoyloxymethyl-indole-1-carboxylic acid tert-butyl ester [CPL-2012-144]

Charged 3-hydroxymethylindole-1-carboxylic acid tert-butyl ester is added in to a flask and added Dimethyl aminopyridine, Triethyl amine and THF at 0° C. Maintained the reaction for 10 Minutes and then added valeric anhydride drop wise slowly at 0° C. and maintained the reaction for 3 hours. After completion of the reaction added citric acid solution to the reaction mixture and stirred well. Extract the reaction mass with ethyl acetate twice. Dried the organic layer over sodium sulfate Concentrated the organic layer at 40° C. Thus obtained residue is chromatographed on silica gel using Hexane as the eluent.

Example 6:
3-Heptanoyloxymethyl-indole-1-carboxylic acid tert-butyl ester [CPL-2012-159]

Charged 3-hydroxymethylindole-1-carboxylic acid tert-butyl ester is added in to a flask and added Dimethyl aminopyridine, Triethyl amine and THF at 0° C. Maintained the reaction for 10 Minutes and then added Heptanoic anhydride drop wise slowly at 0° C. and maintained the reaction for 3 hours. After completion of the reaction added citric acid solution to the reaction mixture and stirred well. Extract the reaction mass with ethyl acetate twice. Dried the organic layer over sodium sulfate and concentrated the organic layer at 40° C. Thus obtained residue is chromatographed on silica gel using Hexane as the eluent.

Example 7:
3-Propionyloxymethyl-indole-1-carboxylic acid benzyl ester [CPL-2013-158]

To a stirred solution of 3-Hydroxymethyl-indole-1-carboxylic acid benzyl ester in THF were added DMAP and Triethyl amine at 0° C. To this stirred reaction mixture propionic anhydride in THF was added maintained the reaction at 25-30° C. for 4 hrs. After completion of the reaction, reaction mass is concentrated thus obtained residue is dissolved in Aqueous Saturated sodium bicarbonate and aqueous layer was extracted with ethyl acetate (twice). Organic layer was washed with 1 NHCl. Organic layer was concentrated to obtain crude material which is further purified over column chromatography (DCM: MeOH).

Example 8: 3-[Hydroxy-(2,4,5-trifluoro-phenyl)-methyl]indole-1-carboxylic acid tert-butyl ester [CPL-2013-156]

Charged 20 ml of THF, magnesium turnings and 2,4,5-Trifluoro bromo benzene in to a round bottom flask. Slowly cooled the reaction mass to −5 to 0° C. Added a solution of N-Boc-indole-carbaldehyde to the reaction mixture. Maintained the reaction at 0° C. for 3 hrs. After completion of the reaction, reaction mass is added to 10% citric acid solution. Reaction mass is extracted using ethyl acetate. Aqueous layer and organic layer separated. Dried the organic layer over sodium sulfate. Distilled the ethyl acetate under vacuum to obtain residue which is further purified over column chromatography (Hexane).

Example 9: 3-(Phenyl-propionyloxy-methyl)-indole-1-carboxylic acid tert-butyl ester [CPL-2013-155]

Charged 3-(Hydroxy-phenyl-methyl)-indole-1-carboxylic acid tert-butyl ester and dimethyl aminopyridine in to a 50 ml of THF. Reaction mass is cooled to 0-5° C. and stirred well for a period of 15 minutes. Added 0.5 ml of propionic anhydride dropwise to the reaction mixture and reaction was monitored by TLC. Reaction was maintained for 3 hrs. After completion of the reaction, THF is distilled out completely and reaction mixture was washed with sodium bicarbonate solution and citric acid solution. Ethyl acetate is added to the reaction mixture and extracted which is further concentrated to yield 3-(Phenyl-propionyloxy-methyl)-indole-1-carboxylic acid tert-butyl ester.

Example 10: 3-[Propionyloxy-(2,4,5-trifluoro-phenyl)-methyl]-indole-1-carboxylic acid tert-butyl ester [CPL-2013-157]

Charged 3-[Hydroxy-(2,4,5-trifluoro-phenyl)-methyl]-indole-1-carboxylic acid tert-butyl ester in to 50 ml of THF. Added 95 mg of Dimethyl aminopyridine in to the reaction mass. Slowly cooled the reaction mass to 0-5° C. and maintained for 15 minutes. Added 0.5 ml of propionic anhydride drop wise to the reaction mixture and reaction was monitored by TLC. Reaction was maintained for 3 hrs. After completion of the reaction, THF is distilled out completely and reaction mixture was washed with sodium bicarbonate solution and citric acid solution. Ethyl acetate is added to the reaction mixture and extracted which is further concentrated to yield 3-[Propionyloxy-(2,4,5-trifluoro-phenyl)-methyl]-indole-1-carboxylic acid tert-butyl ester.

The examples provided herein are for illustrative purpose only and does not limit the scope of the invention as defined in the claims.

General Procedure for Screening:

Evaluated the anti-inflammatory effect of compounds of formula-I using acute paw edema model in Wistar rats using the following procedure.

Procedure:—

All animals will be divided into required number of groups (n=6 per group; 8-12 weeks age) on the basis of body weight. After grouping basal paw volume of all animals will be measured with the help of plethysmometer instrument followed by drug administration by oral route. After 1 hr of dosing 100 µL of 1% Carrageenan prepared in normal saline will be administered in hind paw of all animals by S.C route. After 1 hr of carrageenan dosing paw volume of all animals will be measure up to 6 hr at each 1 hr interval.

To Evaluate Anti-Inflammatory Effect of the Compounds Using FCA Model in Wistar Rats.

Test System: Wistar rats
Sex: Female
No. of animals: 6-8 animals per group
Age: 6-8 Weeks
Randomization: On basis of initial Body weight.
Vehicle: Water for Injection
Dose Volume: 10 ml/kg
Procedure:
1. Arthritis will be induced by sub plantar injection of 0.1 mg of Myco bacterium *butyricum* (FCA) suspended in 0.1 ml of light liquid paraffin into the right hind paw.
2. Paw volume will be measured on Day 0, 1, 7, 10, 14, 21 and 28. If required study will be extended & paw volume will be measure till day 56.
3. Body weight will be measured on Day 0, 7, 14, 21 and 28. If required study will be extended & body weight will be measure till day 56.
4. Animal will be dosed every day in the morning starting from Day 1 to Day 56.
5. On the next day of last paw volume measurement all the animals will be euthanized.

The Results are Tabulated Under:

Accordingly the invention pertains to novel stable derivatives of indole-3-carbinol as described in the detail description are showing potent anti-inflammatory activity.

We claim:
1. A compound of Formula-1:

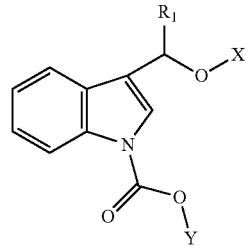

Formula-1 wherein,
$R_1$ is selected from hydrogen, aryl, haloaryl;
X is selected from —$C(O)C_nH_{2n+1}$ wherein n is an integer selected from 2 to 16 or —$C(O)(CH_2)_m$—COOH wherein m is an integer selected from 2 to 5; Y is selected from alkyl or arylalkyl;
or pharmaceutically acceptable salts thereof.

2. A compound as claimed in claim 1, wherein, the compound of Formula-1 is
 3-Hexadecanoyloxymethyl-indole-1-carboxylic acid tert-butyl ester
 or pharmaceutically acceptable salts thereof.

3. The compound as claimed in claim 1 wherein said compound is useful for the treatment of inflammation.

4. A compound as claimed in claim 1, wherein, the compound of Formula-1 is succinic acid mono-(1-tert-butoxycarbonyl-1H-indol-3-ylmethyl) ester or pharmaceutically acceptable salts thereof.

5. A compound as claimed in claim 1, wherein, the compound of Formula-1 is 3-Propionyloxymethyl-indole-1-carboxylic acid tert-butyl ester or pharmaceutically acceptable salts thereof.

6. A compound as claimed in claim 1, wherein, the compound of Formula-1 is 3-Butyryloxymethyl-indole-1-carboxylic acid tert-butyl ester or pharmaceutically acceptable salts thereof.

7. A compound as claimed in claim 1, wherein, the compound of Formula-1 is 3-Pentanoyloxymethyl-indole-1-carboxylic acid tert-butyl ester or pharmaceutically acceptable salts thereof.

8. A compound as claimed in claim 1, wherein, the compound of Formula-1 is 3-Heptanoyloxymethyl-indole-1-carboxylic acid tert-butyl ester or pharmaceutically acceptable salts thereof.

|  | Time | | | | | | |
|---|---|---|---|---|---|---|---|
|  | (−1) 1 hr | 1 hr | 2 hr | 3 hr | 4 hr | 5 hr | 6 hr |
| Control-0 mg/Kg | 100 | 130.36 | 135.93 | 131.83 | 125.82 | 124.44 | 117.22 |
| CPL-2012-136-50 mg/kg | 100 | 117.26 | 121.86 | 123.85 | 121.57 | 119.72 | 111.76 |
| Control-0 mg/Kg | 100 | 127.19 | 132 | 133.22 | 128.8 | 122.82 | 121.23 |
| CPL-2012-139-50 mg/kg | 100 | 116.73 | 123.68 | 122.72 | 120.63 | 115.55 | 113.42 |
| Control-0 mg/Kg | 100 | 116.24 | 131.59 | 128.52 | 125.15 | 121.78 | 119.19 |
| CPL-2012-144-50 mg/kg | 100 | 112.98 | 123.96 | 125.7 | 123.32 | 123.07 | 121.46 |
| Control-0 mg/Kg | 100 | 124.96 | 132.44 | 128.75 | 122.02 | 115.85 | 110.89 |
| CPL-2013-156-50 mg/kg | 100 | 115.2 | 113.62 | 116.25 | 115.73 | 113.69 | 111.56 |
| Control-0 mg/Kg | 100 | 116.52 | 127.58 | 119.54 | 114.35 | 109.38 | 107.04 |
| CPL-2013-158-50 mg/kg | 100 | 113.82 | 115.12 | 112.02 | 112.46 | 108.11 | 107.2 |

9. A compound as claimed in claim 1, wherein, the compound of Formula-1 is 3-Propionyloxymethyl-indole-1-carboxylic acid benzyl ester or pharmaceutically acceptable salts thereof.

10. A compound as claimed in claim 1, wherein, the compound of Formula-1 is 3-(Phenyl-propionyloxy-methyl)-indole-1-carboxylic acid tert-butyl ester or pharmaceutically acceptable salts thereof.

11. A compound as claimed in claim 1, wherein, the compound of Formula-1 is 3-[Propionyloxy-(2,4,5-trifluoro-phenyl)-methyl]-indole-1-carboxylic acid tert-butyl ester or pharmaceutically acceptable salts thereof.

* * * * *